United States Patent
Klausen et al.

(10) Patent No.: US 10,226,323 B2
(45) Date of Patent: Mar. 12, 2019

(54) DOUBLE CONE BIODEGRADABLE FILTER

(71) Applicant: Cook Medical Technologies LLC, Bloomington, IN (US)

(72) Inventors: Kasper Klausen, Lille Skensved (DK); Steen Aggerholm, St. Heddinge (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 189 days.

(21) Appl. No.: 15/293,473

(22) Filed: Oct. 14, 2016

(65) Prior Publication Data
US 2017/0105831 A1   Apr. 20, 2017

Related U.S. Application Data

(60) Provisional application No. 62/242,392, filed on Oct. 16, 2015.

(51) Int. Cl.
| *A61F 2/01* | (2006.01) |
| *A61F 2/89* | (2013.01) |
| *A61F 2/90* | (2013.01) |

(52) U.S. Cl.
CPC .............. *A61F 2/01* (2013.01); *A61F 2/89* (2013.01); *A61F 2/90* (2013.01);
(Continued)

(58) Field of Classification Search
CPC .............. A61F 2/01; A61F 2002/011; A61F 2002/016; A61F 2002/018; A61F 2/013;
(Continued)

(56) References Cited

U.S. PATENT DOCUMENTS

| 8,668,713 B2 | 3/2014 | Horan et al. |
| 9,005,269 B2 | 4/2015 | Armstrong et al. |
| (Continued) | | |

FOREIGN PATENT DOCUMENTS

| CN | 204411025 | 6/2015 |
| WO | WO 2008/010197 A2 | 1/2008 |
| (Continued) | | |

OTHER PUBLICATIONS

Extended European Search Report for Application No. 16193974.9-1651, dated Dec. 20, 2016.
(Continued)

*Primary Examiner* — Katrina Stransky
(74) *Attorney, Agent, or Firm* — Brinks Gilson & Lione

(57) ABSTRACT

The present disclosure provides for a double cone filter and a delivery apparatus for deploying the filter within the body. The filter may have superior and inferior rings connected to each other by a plurality of connectors. The rings may have a first degradation rate, and the connectors may have a second degradation rate. The second degradation rate may be faster than the first degradation rate, such that the connectors degrade faster than the rings. In this way, the filter has a filtering state when the connectors are present. After the connectors degrade or partially degrade, the rings may relax against the vessel wall in an open state. After a sufficient length of time, the rings also degrade such that the filter is completely removed from the body.

21 Claims, 7 Drawing Sheets

(52) U.S. Cl.
CPC ... *A61F 2002/011* (2013.01); *A61F 2002/016* (2013.01); *A61F 2210/0004* (2013.01); *A61F 2230/005* (2013.01); *A61F 2230/0078* (2013.01); *A61F 2250/003* (2013.01)

(58) Field of Classification Search
CPC ........ A61F 2210/0004; A61F 2250/003; A61F 2230/005; A61F 2/89; A61F 2/90
See application file for complete search history.

(56) References Cited

U.S. PATENT DOCUMENTS

| | | | |
|---|---|---|---|
| 2008/0027481 A1* | 1/2008 | Gilson | A61F 2/01 606/200 |
| 2008/0188887 A1* | 8/2008 | Batiste | A61F 2/01 606/200 |
| 2010/0185230 A1* | 7/2010 | Horan | A61F 2/01 606/200 |
| 2010/0268262 A1 | 10/2010 | Balar | |
| 2011/0152919 A1 | 6/2011 | Chin | |
| 2011/0213404 A1* | 9/2011 | Binkert | A61F 2/01 606/200 |
| 2011/0224715 A1 | 9/2011 | Chin et al. | |
| 2012/0083822 A1* | 4/2012 | Anukhin | A61F 2/01 606/200 |
| 2015/0133990 A1* | 5/2015 | Davidson | A61N 1/378 606/200 |

FOREIGN PATENT DOCUMENTS

| | | |
|---|---|---|
| WO | WO 2010/025775 A1 | 3/2011 |
| WO | WO 2014100375 | 6/2014 |
| WO | WO 2014/0140088 A2 | 9/2014 |

OTHER PUBLICATIONS

Thors, Axel, et al., "Resorbable inferior vena cava filters: trial in an invivo porcine model," Journal of vascular and interventional radiology: JVIR 22.3 (Mar. 2011): 330-5.

* cited by examiner

DOUBLE CONE BIODEGRADABLE FILTER

CROSS-REFERENCE TO RELATED APPLICATIONS

This application claims the benefit of priority under 35 U.S.C. § 119(a) to U.S. Provisional Application No. 62/242,392, filed Oct. 16, 2015, which is hereby incorporated by reference in its entirety.

BACKGROUND

1. Field of the Invention

The present disclosure relates to medical devices. More particularly, the disclosure relates to a double cone, biodegradable filter and an assembly for delivery and retrieval of the filter.

2. Background

Blood filters are common prophylactic devices to prevent pulmonary embolisms caused by deep vein thrombosis, often placed within body vessels. Such filters can be placed using minimally invasive techniques, either from the jugular or femoral vein. Current filters often are only needed for a short period of time, but are rarely removed because such removal may require a secondary procedure that many patients may avoid. However, if filters are left in the body vessel, they may cause unintended consequences long after their utility has passed.

As such, there is a need for further filters that may be placed in a body vessel and used for a short period of time, but eventually are completely removed from the body vessel, operating as a temporary filter.

BRIEF SUMMARY OF THE INVENTION

This disclosure may include any of the following embodiments in various combinations and may also include any other aspect described below in the written description or in the attached drawings.

The present disclosure provides for a filter for use in a body vessel having a longitudinal axis. The filter may include a superior ring including a plurality of superior struts having a first superior strut extending to a second superior strut, defining a first superior valley. The filter may also include a third superior strut extending to a fourth superior strut, defining a second superior valley. The superior ring may have first superior valleys alternating with second superior valleys.

The filter may also have an inferior ring including a plurality of inferior struts having a first inferior strut extending to a second inferior strut, defining a first inferior peak. The filter may also include a third inferior strut extending to a fourth inferior strut, defining a second inferior peak. The inferior ring may have first inferior peaks alternating with second inferior peaks.

The filter has a plurality of connectors extending between the superior and inferior rings. The plurality of connectors may have a degradation rate greater than or faster than that of the superior ring and that of the inferior ring. Each connector has a first end extending to a second end with a central region therebetween. The connectors cross each other and in some embodiments may be in contact with each other at the respective central regions The second degradation rate (e.g. possibly formed by a second degradation profile) may be greater or faster than the first degradation rate such that the connectors degrade before the rings. This may give the filter a filtering state and an open state. The first and second superior valleys and first and second inferior peaks extend toward the respective central regions in the filtering state. The first and second superior valleys and the first and second inferior peaks may contact the body vessel or its wall in the open state.

To degrade at different times, the superior and inferior rings may have a first biodegradable material and the plurality of connectors comprise a second biodegradable material such that the plurality of connectors degrade before the superior and inferior rings to move the filter from the filter state to the open state. The first biodegradable material may have an inner core and an outer layer.

Alternatively, the superior and inferior rings comprise a first biodegradable material having a first size and the plurality of connectors comprise the first biodegradable material having a second size wherein the second size is smaller than the first size. In this way, the plurality of connectors may degrade before the superior and inferior rings to move the filter from the filter state to the open state.

In one embodiment, each first superior valley may have one first end attached to and parallel with the first superior strut and extending to the second end being attached to and parallel with one second inferior strut. All connectors may be arranged in this manner.

In another embodiment, which may be separate or in combination with other embodiments, the first superior strut and the second superior strut each have a first superior length. The third superior strut and the fourth superior strut each have a second superior length such that the first superior length is greater than the second superior length. Likewise, the first inferior strut and the second inferior strut each have a first inferior length. The third inferior strut and the fourth inferior strut each have a second inferior length such that the first inferior length is greater than the second inferior length.

In one embodiment, the plurality of connectors is woven, contacting, or laced with each other at the respective central regions such that a first connector moves relative to a second connector. Alternatively, the plurality of connectors is immobilized relative to each other at the respective central regions such that a first connector does not move relative a second connector. The connectors are immobilized by bonding or welding.

The first and second superior valleys may form a first truncated cone having a large superior base and a small superior base in the filtering state. Likewise, the first and second inferior peaks form a second truncated cone having a large inferior base and a small inferior base in the filtering state. The large superior and inferior bases may be parallel to each other, the small superior and inferior bases may be parallel to and facing each other.

The first superior valleys extend a first distance toward the respective central regions in the filtering state and the second superior valleys extend a second distance toward the respective central regions in the filtering state such that the first distance is less than the second distance. Similarly, the first inferior peaks extend a first distance toward the respective central regions in the filtering state and the second inferior peaks extend a second distance toward the respective central regions in the filtering state such that the first length is less than the second length.

This disclosure also provides for an assembly for delivery and retrieval having a sheath, an inner member, and a filter as described here. The sheath may have a body extending from a proximal part to a distal part, the body being tubular and forming a lumen extending therethrough. The inner member may extend from a proximal portion to a distal portion, the inner member being disposed within the lumen and slidably movable relative to the sheath. The filter may be removably coupled to the distal portion.

As one possible advantage of the above described filter, the filter will operate as a temporary filter having an overall filter degradation profile in which the connectors may degrade first, the rings may degrade second, and both the connectors and the rings are to be absorbed in the body over time. In other words, the connectors may degrade first, and then the rings may degrade at a later time. Both will be removed from the body vessel after a predetermined period of time without the need for a secondary surgical procedure.

And another possible advantage of the above described filter, the first and second superior valleys and the first and second inferior peaks all extend toward the respective central regions. This may assist in filtering capacity, in addition to the connectors. These structures provide increased filtering capacity when in the filtering state.

As another possible advantage of the above described filter, the superior and inferior rings may have struts of different lengths (e.g. first and second superior lengths and first and second inferior lengths). This geometry gives the filter greater flexibility to respond to natural body movements, such as breathing and heartbeat. This flexibility also prevents the filter from fatiguing over time. The present disclosure may be better understood by referencing the accompanying figures.

DETAILED DESCRIPTION

The present disclosure will now be described more fully with reference to the accompanying figures, which show preferred embodiments. The accompanying figures are provided for general understanding of the structure of various embodiments. However, this disclosure may be embodied in many different forms. These figures should not be construed as limiting and they are not necessarily to scale.

The following definitions will be used in this application.
"About" or "substantially" mean that a given quantity is within 10%, preferably within 5%, more preferably within 1%, of a stated value.
"Biodegrade" and variations thereof means that the material will be absorbed and excreted by the body over time, being synonymous with bioresorbable and bioabsorbable.

Figure 1A:
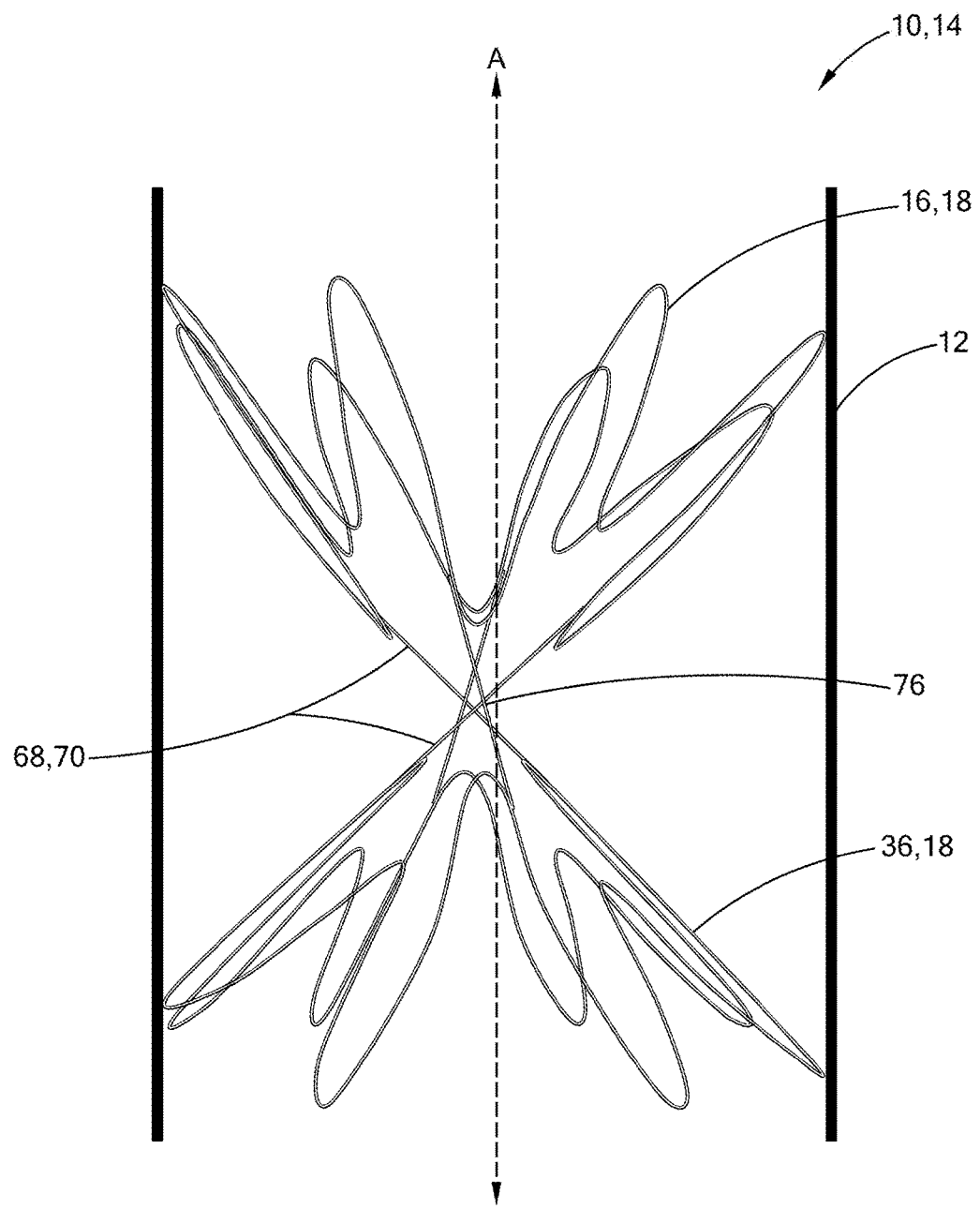
FIGS. 1A-B depict side views of a filter in accordance with one embodiment of the present invention.
Figure 1B:
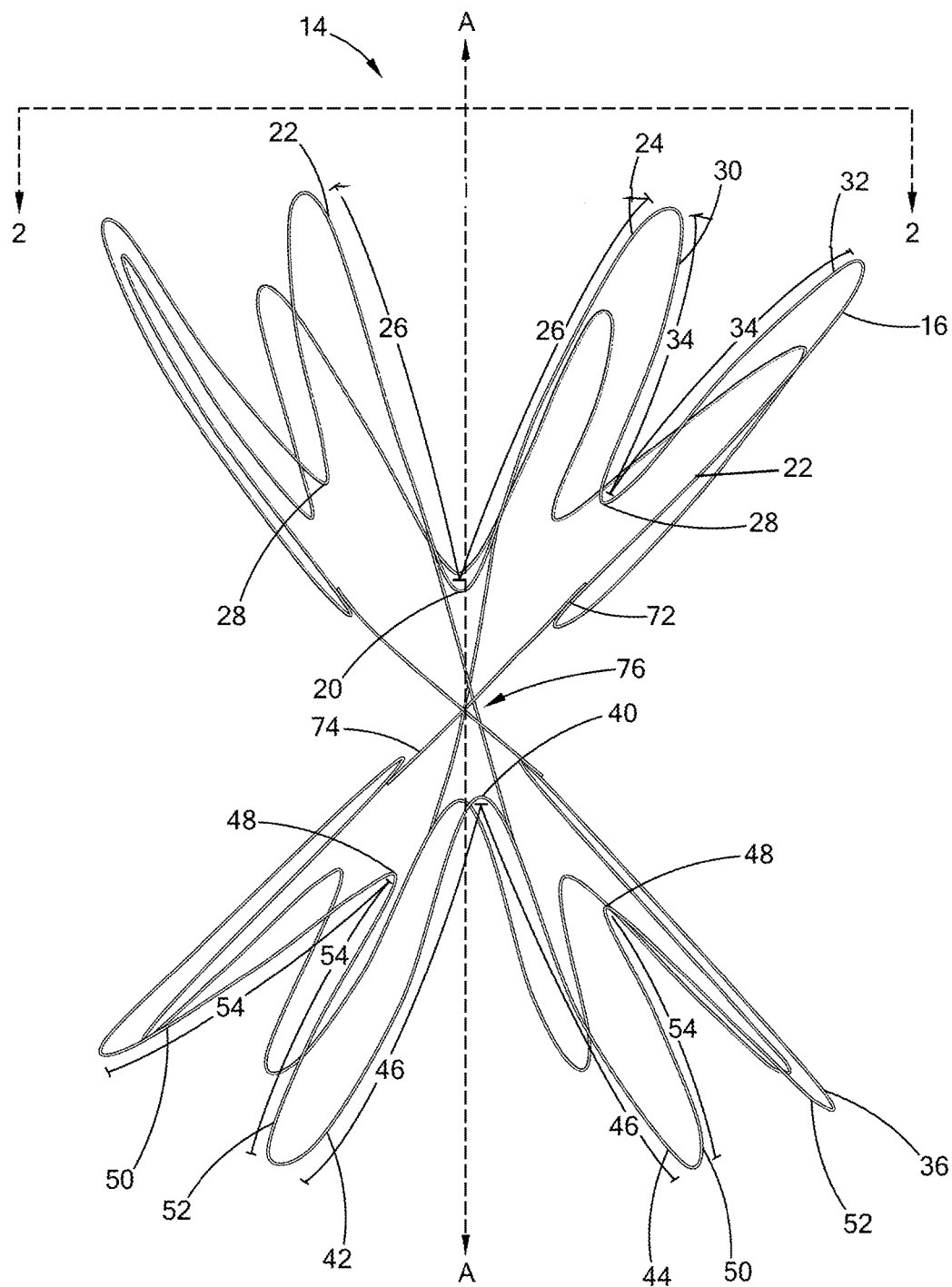

FIGS. 1A-B depict views of a dual conical filter 14 in accordance with one embodiment of the present disclosure. For example, FIG. 1A depicts the filter having a superior ring 16 made with a first degradation rate 18 and an inferior ring 36 made with the first degradation rate 18. The filter is placed within a body vessel 10 having a vessel wall 12. The first degradation rate may be formed with, or through the use of, a first biodegradable material.

The superior and inferior rings (16, 36) are positioned along a longitudinal axis A having a plurality of connectors 68 therebetween. The connectors 68 are made with a second degradation rate 70. The second degradation rate 70 may be greater or faster than the first degradation profile such that the superior and inferior rings degrade at a second time and plurality of connectors biodegrading at a first time before the second time. This results in faster degradation of the connectors to move the filter from a filtering state to an open state.

Although the connectors 68 serve to connect the two rings of the device (in some embodiments, the superior ring 16 and the inferior ring 36), in certain embodiments the connectors 68 may serve to filter blood as it flows through the device 10.

As discussed herein, the overall filter degradation profile may have the connectors degrading at a higher rate of speed than the rings. The rings may degrade at approximately the same rate of speed as each other. This may be achieved in one or more ways. For example, the inventors are able to achieve the overall filter degradation profile by using different biodegradable materials (e.g. first and second biodegradable materials). The second biodegradable material (used for the connectors) may degrade faster than the first biodegradable material (used for the rings). The first and/or second biodegradable materials may also each employ a combination of materials, being in the form of polymer combinations, alloy combinations, coatings, protective agents, corrosion inhibitors, corrosion induces, and the like.

In one example, the inventors envision using a polymer layer applied to the superior and inferior rings to tailor the degradation profile. In one embodiment, a layer of polymer over the metal wire of the rings may serve to slow degradation. The inventors also envision galvanic corrosion or surface treatment to tailor the degradation profile of the connector wires. This may cause the connectors to degrade faster.

In another embodiment, the superior and inferior rings may be made of a first metal or first metal alloy, and the connectors may be made of a second metal or second metal alloy. In this embodiment, the second metal or alloy of the connectors has a composition such that it serves as a galvanic anode compared to the first metal or alloy. In this way, the connectors degrade first, serving as a galvanic protection mechanism for the remainder of the device. When the connectors degrade, the device then transitions to the open configuration, and with the first metal no longer galvanically protected, the rings begin to biodegrade while in the open configuration.

In one embodiment, both the first and second biodegradable materials are metals or metal alloys. Such metals and metal alloys may be selected from a variety of materials, including but not limited to iron, magnesium, manganese, zinc, calcium, and rare earth metals. As described herein, a first biodegradable material may be considered distinct from a second biodegradable material even when the two materials have the same elemental constituents. For example, a first material may be made of iron and manganese, with manganese constituting about 35% of the weight of the alloy, and a second material may be made of iron and manganese, with manganese constituting about 40% of the alloy by weight. These are considered two different materials.

Alternatively, the first and second degradation rates could be achieved by using the same biodegradable material for the rings and connectors. However, in this case, the connectors may be formed with a different size, less material volume, different surface qualities, and the like, such that they degrade faster than the rings. In one embodiment, the difference in size between the wire of the connectors and the wire of the rings may be a difference in thickness. For example, the connectors may be made of a wire of lower thickness (or lower diameter) than the wire of at least one of the inferior and superior ring.

In another example, the inventors envision forming the connectors of substantially the same thickness, or even a relatively thicker wire size, compared to the rings. After forming the connectors, the connectors would undergo etching (including, in one embodiment, chemical etching) or grinding in their center regions to create a weaker area having the second degradation rate. In certain embodiments, such etching or grinding might result in a metal having less of a protective oxide layer on its exterior. In other embodiments, the uneven surface generated by etching or grinding might serve as a focal point for the initiation of degradation. In this way, the bonding points of the connectors to the rings would be thicker and stronger, while the connectors themselves would degrade faster than the rings.

While the text herein provides some exemplary ways to form the different degradation rates, these examples are not intended to be limiting. Those skilled in this art could envision other methods, manners, and structures to form the different degradation rates without falling beyond the scope and spirit of this disclosure.

The dual conical filter 14 may be symmetrical to provide greater stability within the body vessel 10. In addition, the dual conical filter 14 may be convertible from the filtering state to the open state such that the open state does not substantially affect normal blood flow. The details of the open and close state will be discussed further below.

In addition, by tailoring the material and degradation rate within the dual conical filter 14, the user may control the time that the filter spends in the filtering state versus the open state.

FIG. 1B shows further details of the dual conical filter. For example, the superior ring 16 comprises a plurality of superior struts having a first superior strut 22 extending to a second superior strut 24, defining a first superior valley 20. The superior ring 16 also has a third superior strut 30 extending to a fourth superior strut 32, defining a second superior valley 28. The superior ring 16 has a first superior valleys (e.g. 20) alternating with the second superior valleys (e.g. 28).

FIG. 1B also shows the inferior ring 36 having a plurality of inferior struts being a first inferior strut 42 extending to a second inferior strut 44, defining a first inferior peak 40. A third inferior strut 50 extends to a fourth inferior strut 52, defining a second inferior peak 48. The inferior ring 36 has first inferior peaks (e.g. 40) alternating with second inferior peaks (e.g. 48).

The filter 14 also has a plurality of connectors extending between the superior and inferior rings (16, 36). The plurality of connectors is formed with a faster degradation rate than the rings, possibly through the use of the second biodegradable material having the second degradation profile. Each connector has a first end 72 extending to a second end 74, with a central region 76 therebetween. The plurality of connectors are in contact with each other at the respective central regions.

In one embodiment, when materials are selected such that the connectors galvanically protect the rings from degradation, the entire connector from first end 72 to second end 74, including central region 76, may be made of an anodic material. In another embodiment, only a portion of the connector, such as at its apices (at either the first end 72 or the second end 74) may be made of the anodic material. In another embodiment, a coil of anodic material (not shown) may be placed across each ring 16, 18 of the device 10 in order to galvanically protect each ring.

The rings and connectors make it possible for the filter 14 to have a filtering state and an open state such that the first and second superior valleys (20, 28) and the first and second inferior peaks (40, 48) extend toward the respective central regions 76 in the filtering state. Similarly, the first and second superior valleys (20, 28) and the first and second inferior peaks (40, 48) contact the vessel wall in the open state (shown in FIG. 5B).

The superior ring 16 and the inferior ring 36 may contain struts of different lengths. For example the first superior strut 22 and the second superior strut 24 may each have a first superior length 26. Likewise, the third superior strut 30 and the fourth superior strut 32 may each have a second superior length 34 such that the first superior length 26 is greater than the second superior length 34.

Likewise in the inferior ring 36, the first inferior strut 42 and the second inferior strut 44 may each have a first inferior length 46. The third inferior strut 50 and the fourth inferior strut 52 may each have a second inferior length 54 such that the first inferior length 46 is greater than the second inferior length 54. The first inferior length 46 may be substantially equal to the first superior length 26. The second inferior length 54 may be substantially equal to the second superior length 34. With this geometry, the filter is symmetrical.

Having different strut lengths result in the loaded stress primarily being on the longer struts of the rings. This arrangement creates less permanent deformation of the filter. In addition, having filtration struts arranged in this manner of different lengths result in a low risk of entanglement of the struts and a well-defined distribution of the struts around the body vessel.

In one embodiment, the first superior length 26 and the first inferior length 46 are about 25 millimeters ("mm"). The second superior length 34 and the second inferior length 54 are about 17.5 millimeters. The distance between the bend regions of or adjacent to the first superior strut 22 and the second superior strut 24 may be about the same distance as between the first inferior strut 42 and the second inferior strut 44 at the respective bend regions. Similarly, the distance between the third superior strut 30 and the fourth superior strut 32 at the respective bend regions may be about the same distance as between the third inferior strut 50 and the fourth inferior strut 52 at the respective bend regions.

In FIG. 1B, each first superior valley 20 may have one first end 72 attached to and parallel with the first superior strut 22 and extending to the second end 74, being parallel to and attached with one second inferior strut 44. This geometry creates an overlapping region between the valleys or peaks with the connectors.

Of course, one skilled in the art will understand that is may be possible to have the connectors connect to the second superior valleys (e.g. 28) and extend to the second inferior peaks (e.g. 48). In this manner, one first end 72 may attach to and be parallel with the third superior strut 30 and extend to the second end 74, being parallel to and attached with one fourth inferior strut 52. This attachment may repeat or propagate around the ring with each connector to create the hourglass shape.

Figure 2A:
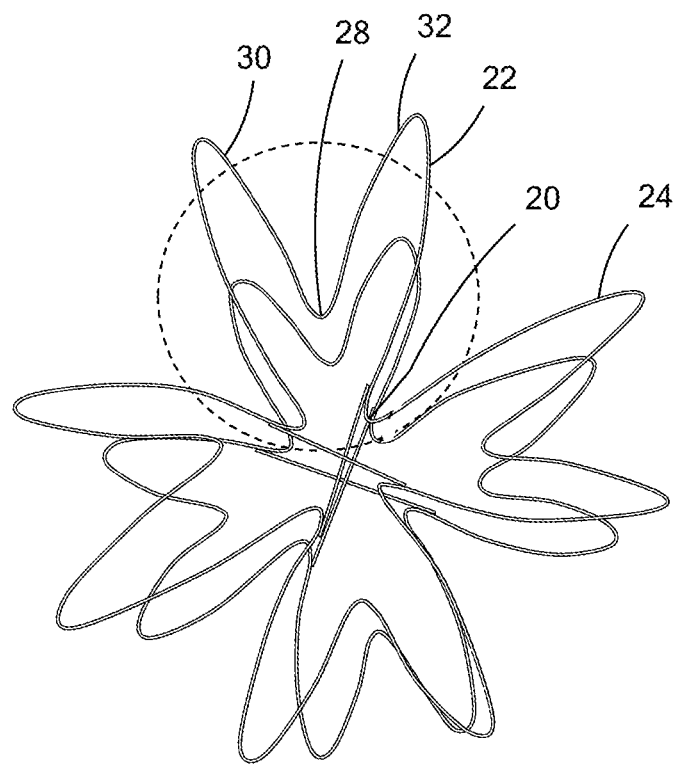
FIGS. 2A-B depict end views of the filter of FIG. 1B.
Figure 2B:
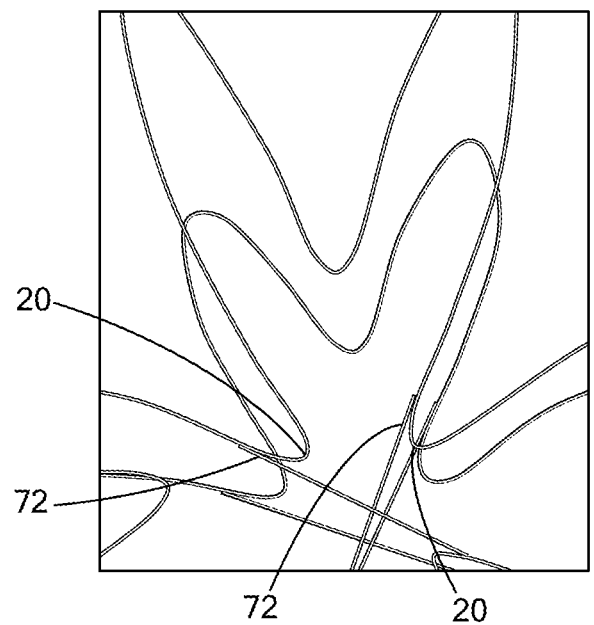

Details of this overlap are also shown in FIGS. 2A-B. Line 2-2 in FIG. 1B depicts an end view of the filter, shown in FIGS. 2A-B. The third superior strut 30 extends to the fourth superior strut 32, defining the second superior valley 28. Likewise, the first superior strut 22 extends to the second superior strut 24, defining the first superior valley 20. The dotted circle region is blown up in FIG. 2B.

Here, the first end 72 overlaps with the first superior strut of the first superior valley 20. As shown in this figure, this arrangement may be the same for every first superior valley in the superior ring. Alternatively, the filter may not have these overlapping regions and instead the superior ring could be cut from a uniform tube with the connectors such that there is no overlap.

Figure 3:
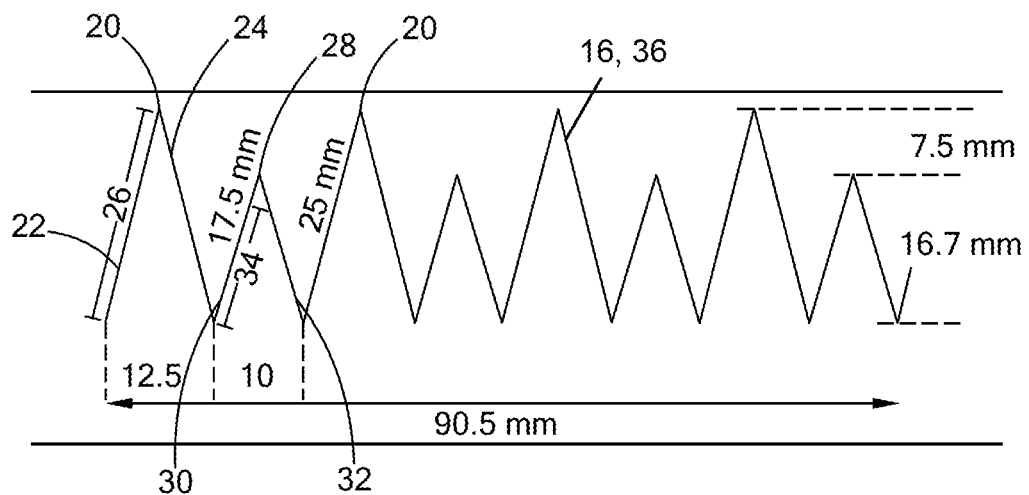
FIG. 3 depicts a superior ring of the filter of FIG. 1B.

FIG. 3 shows a superior ring, having a first superior strut 22 and a second superior strut 24, each having the first superior length 26. This length may be about 25 mm. Also shown is the third superior strut 30 and the fourth superior strut 32, each having a second superior length 34, being about 17.5 mm. In this view, the superior ring 16, which could also be an inferior ring 36, is detached at its ends and elongated such that the total span could be 90.5 mm. Of course, the total length may be longer when considering each strut. In addition, these length quantities are estimates and should not be taken to limit the scope of possible lengths. Any quantity is within the scope of this disclosure. In FIG. 3, one of skill in this art will understand that the ends could be bonded together by any method known in the art, such as gluing, welding, and the like. Alternatively, the rings could be stamped or cut from a tube such that no bonding is required.

The connectors cross each other at their respective central regions. In the previously described aspects of the filter (e.g. FIG. 1B), the plurality of connectors are shown contacting and laced with each other at the respective central regions such that a first connector moves relative to a second connector. As the body moves, this type of lacing puts the plurality of connectors in contact with each other but it does not link or immobilize them at this point relative to each other. The movement of the first connector relative to the second connector could accommodate natural physiological movement (e.g. heartbeat).

Additionally, because the connectors could rub against each other at the central regions, they may start to degrade at the center regions before degrading at any other point in the connectors. This could result in the connectors breaking apart at the central regions during degradation such that each of the superior and inferior rings relaxes against the vessel wall while retaining small pieces of connector at the first superior valleys and first inferior peaks. This could create an intermediate state between the filtering and the open state where the connectors have not fully degraded, but they are not providing filtering capacity.

Alternatively, manufacturing of this device may include laser welding of the connectors to the respective first superior valleys and first inferior peaks. Laser welding could cause the connectors to begin biodegradation at the laser welded regions. This would result in the connector ends separating from one of the rings, and not breaking generally in half during degradation (e.g. in an intermediate state).

Figure 4:
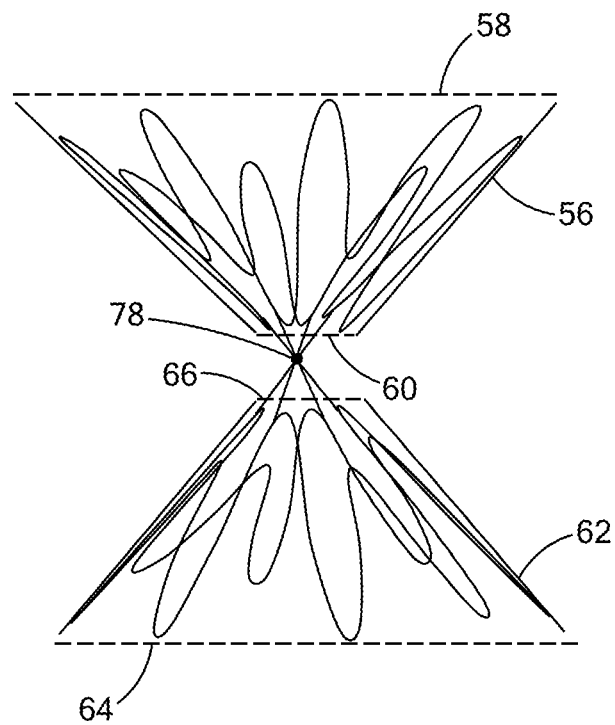
FIG. 4 depicts a side view of a filter in accordance with another embodiment of the present invention.

FIG. 4 shows an alternative embodiment of the dual conical filter where the central regions are bonded together with a welding material 78. The welding material 78 may immobilize the plurality of connectors relative to each other at the respective central regions such that the first connector does not move relative to the second connector.

FIG. 4 also shows the first and second superior valleys forming a first truncated cone 56 having a large superior base 58 and a small superior base 60. Likewise, the first and second inferior peaks form a second truncated cone 62 having a large inferior base 64 and a small inferior base 66, in the filtering state. The large superior and inferior bases (58, 64) are parallel to each other, and the small superior and inferior bases (60, 66) are parallel to and facing each other.

Figure 5B:
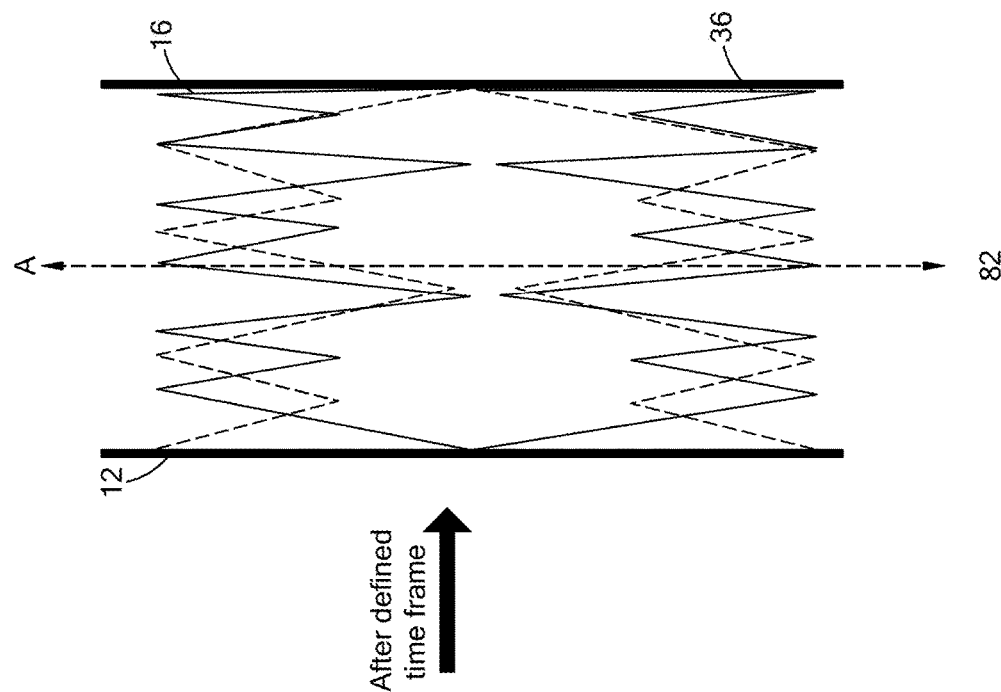
FIGS. 5A-B depict steps of a method of use of the filters of FIGS. 1B and 4.
Figure 5A:
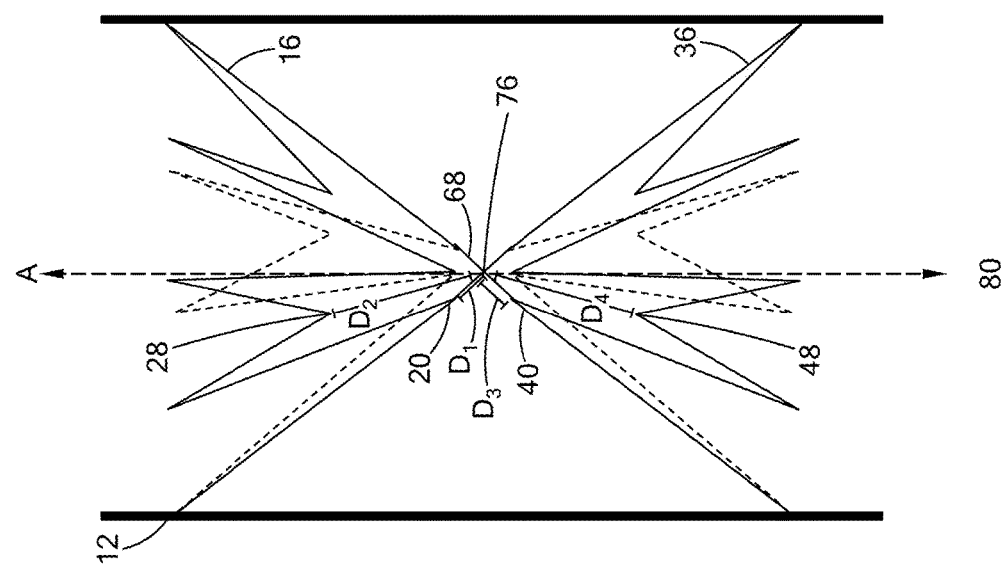

Turning to FIGS. 5A-B, FIG. 5A depicts the filtering state 80 and FIG. 5B depicts the open state 82. As shown, the filtering state 80 affects normal blood flow by extending into the body vessel lumen, while the open state 82 does not substantially affect normal blood flow, not substantially extending into the body vessel lumen. The first superior valleys 20 extend a first distance $D_1$ toward the respective central regions 76 in the filtering state 80. The second superior valleys 28 extend a second distance $D_2$ toward the respective central regions 76 such that the first distance $D_1$ is less than the second distance $D_2$.

Likewise, the first inferior peak 40 extends a third distance $D_3$ towards the respective central region 76 in the filtering state 80. The second inferior peak 48 extends a fourth distance $D_4$ for toward the respective central regions 76 in the filtering state 80 such that the third distance $D_3$ is less than the fourth distance $D_4$.

In this filter, the open state may not be limited to degradation of another attached piece or ring, but rather degradation of the plurality of connectors 68 (FIGS. 5A-B). Upon degradation, the superior and inferior rings (16, 36) open and relax against the vessel wall 12. At this point, they will be endothelialized and will slowly be absorbed by the body.

Such materials that may comprise the first and second biodegradable materials are polymers that may have different biodegradation times in the body. For example, poly-L, D-lactide, polyglycolide, or a co-polymer thereof. In addition, the filter may employ biodegradable metals, such as an alloy of magnesium, zinc, manganese, calcium, and/or iron. The materials listed in this application may also include a combination of different materials to achieve and/or control galvanic coating or corrosion to better control the degradation profiles, as desired.

In one embodiment, the filter may be in place for about 1 to about 4 months, including for about 3 months, in the filtering state. In this timeframe, the filter transforms into the open state, over about 0.5 to about 3 months, or about 0.5 to about 1 month, through degradation of the connectors. Lastly, the rings degrade over 1 to 3 years by degradation of the rings. The total process takes about a minimum of approximately 1 year to a maximum of approximately 3 years. The connectors may degrade faster than the rings by being of a smaller diameter or by having a different, faster degradation profile.

Additionally, to aid in placement of the filter and avoid translocation, the filter may employ barbs attached to the rings and embedded into the vessel wall (not depicted). These barbs may be placed in any suitable place on the filter to contact the vessel wall when in use, and may be formed of the first biodegradable material to degrade with the rings. The barbs may be positioned on one end or both ends of the filter.

The overall size of the rings may be about 15 to 30 mm in diameter when in the open state. When the rings are in the filtering state, they may have a largest diameter of about 30 to about 50 mm. The height of the rings may be about 10 to about 30 mm. The height of the overall filter may be about 70 mm. Of course, these quantities are estimates only and not intended to be limiting. Other quantities are possible.

Figure 6A:
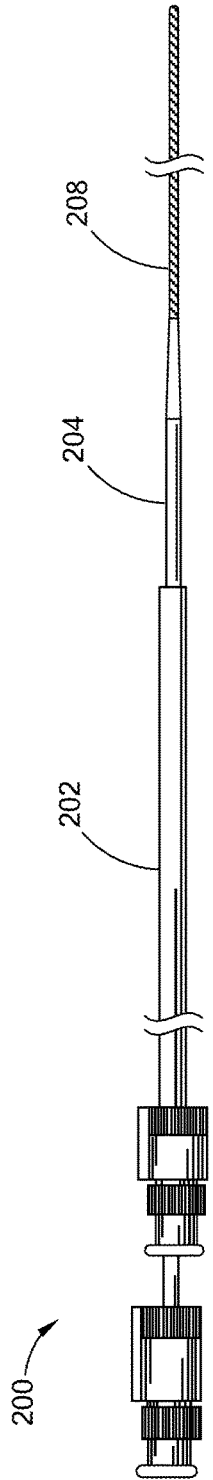
FIGS. 6A-B depict a delivery assembly for the filters of FIGS. 1B and 4 in accordance with one embodiment of the present invention.
Figure 6B:
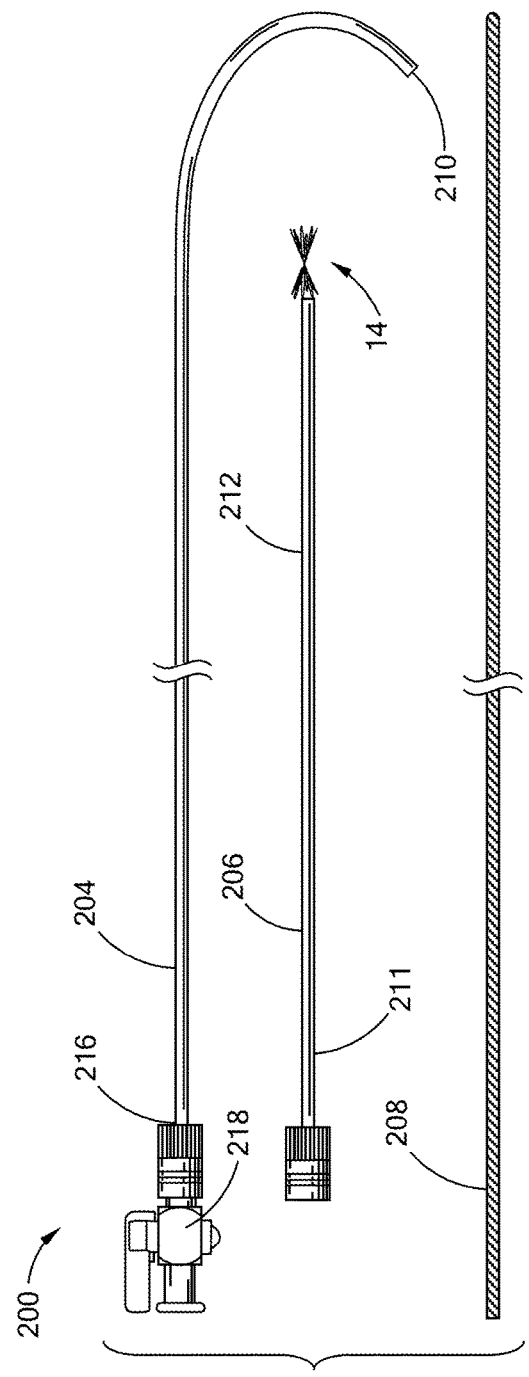

FIGS. 6A-B depict a delivery assembly according to the present disclosure. The device 14 may be delivered or retrieved by way of the Seldinger technique. As shown, the delivery assembly 200 includes an introducer sheath 202 for percutaneously introducing an outer sheath 204 into a body vessel. Of course, any other suitable material for the introducer sheath 202 may be used without falling beyond the scope or spirit of the present disclosure.

The introducer sheath 202 may have any suitable size, for example, between about 5-FR to 17-FR. The introducer sheath 202 serves to allow the outer sheath 204 and an inner member or catheter 206 to be percutaneously inserted to a desired location in the body vessel. The inner member may also include, for example, a stylet. The introducer sheath 202 receives the outer sheath 204 and provides stability to the outer sheath 204 at a desired location of the body vessel. For example, the introducer sheath 202 is held stationary within a common visceral artery, and adds stability to the outer sheath 204, as the outer sheath 204 is advanced through the introducer sheath 202 to a treatment area in the vasculature. The outer sheath 204 has a body extending from a proximal end 216 to a distal end 210, the body being tubular and including a sheath lumen extending therethrough.

As shown, the assembly 200 may also include a wire guide 208 configured to be percutaneously inserted within the vasculature to guide the outer sheath 204 to the treatment area. The wire guide 208 provides the outer sheath 204 with a path to follow as it is advanced within the body vessel. The size of the wire guide 208 is based on the inside diameter of the outer sheath 204 and the diameter of the target body vessel.

A needle may also be used. The needle may be used for percutaneously introducing the wire guide into the patient's body through an access site. A cutting device 14 may also be used to expand the access site. The device may be placed from either the jugular or femoral access points and may use angiographic to visualize it during placement.

When the distal end 210 of the outer sheath 204 is at the desired location in the body vessel, the wire guide 208 is removed and the device 14, having a proximal segment contacting a distal portion 212 of the inner catheter 206, is inserted into the outer sheath 204. The inner catheter 206 is advanced through the outer sheath 204 for deployment of the device 14 through the distal end 210 to treat the body vessel. The catheter 206 extends from a proximal portion 211 to a distal portion 212 and is configured for axial movement relative to the outer sheath 204.

In this example, the distal portion 212 is shown adjacent to the device. Thus, before deployment, the device 14 is coaxially disposed within the lumen of the outer sheath 204 and removably coupled to the distal portion 212 of the catheter 206, or in the alternative, the device 14 is merely pushed by, but not coupled to, the distal portion 212 of the catheter 206.

The outer sheath 204 further has a proximal end 216 and a hub 218 to receive the inner catheter 206 and device 14 to be advanced therethrough. The size of the outer sheath 204 is based on the size of the body vessel in which it percutaneously inserts, and the size of the device 14.

In this embodiment, the device 14 and inner catheter 206 are coaxially advanced through the outer sheath 204, following removal of the wire guide 208, in order to position the device 14 in the body vessel. The device 14 is guided through the outer sheath 204 by the inner catheter 206, preferably from the hub 218, and exits from the distal end 210 of the outer sheath 204 at a location within the vasculature where occlusion is desired. Thus, the device 14 is deployable through the distal end 210 of the outer sheath 204 by means of axial relative movement of the catheter 206. In order to more easily deploy the device 14 into the body vessel, the device 14 may have a lubricious coating, such as silicone or a hydrophilic polymer, e.g. AQ® Hydrophilic Coating as known in the art.

Likewise, in this embodiment the device 14 may also be retrieved by positioning the distal end 210 of the outer sheath 204 adjacent the deployed device in the vasculature. The inner catheter 206 is advanced through the outer sheath 204 until the distal portion 212 protrudes from the distal end 210 of the outer sheath 204. The distal portion 212 is coupled to a proximal end of the device 14, after which the inner catheter 206 is retracted proximally, drawing the device 14 into the outer sheath 204.

The device 14 has a collapsed state for delivery and an expanded state for filtering once delivered to the desired location in the body vessel. In the collapsed state, the device 14 is disposed inside the delivery assembly. The device 14 may be self-expanding or expandable to the expanded state upon exiting the delivery assembly for filtering (as shown partially expanded in FIG. 6B).

The assembly described above is merely one example of an assembly that may be used to deploy the device in a body vessel. Of course, other apparatus, assemblies and systems may be used to deploy any embodiment of the device without falling beyond the scope or spirit of the present disclosure.

Figure 7:
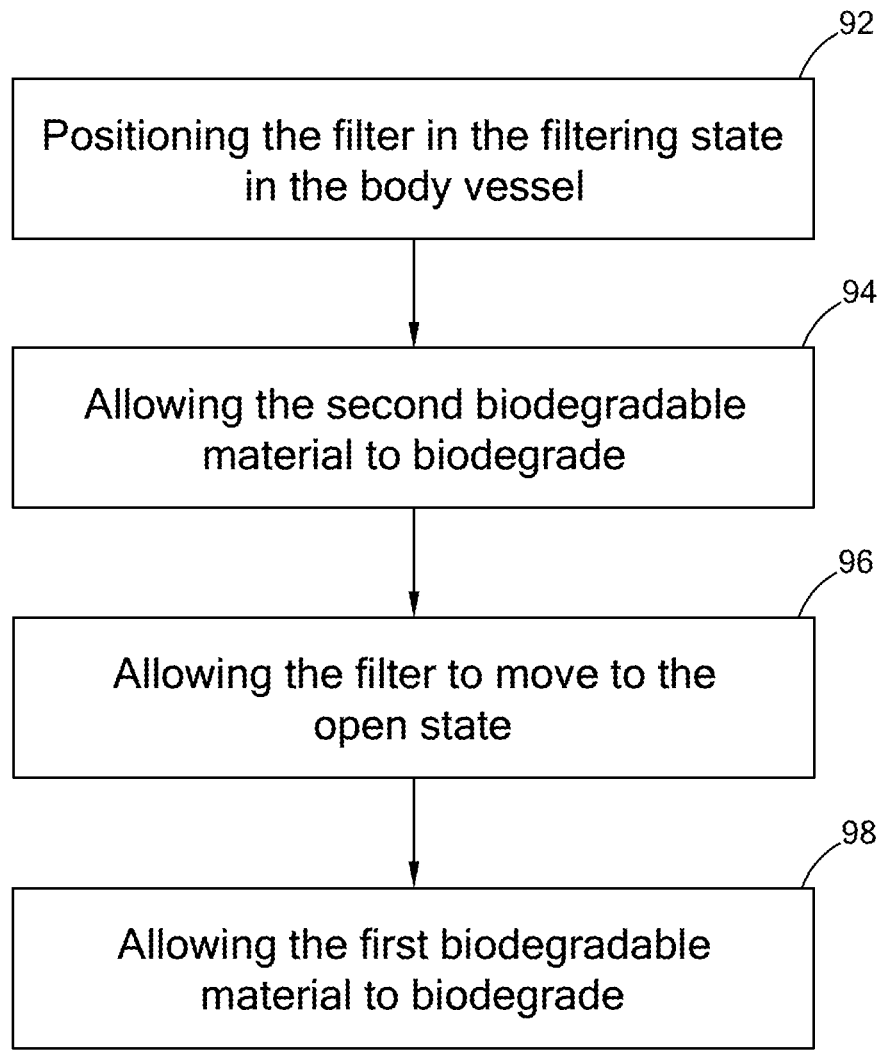
FIG. 7 depicts a flow diagram of a method of use of the filter of FIGS. 1B and 4 in accordance with one embodiment of the present invention.

FIG. 7 depicts steps of a method of use of the filter in accordance with the present disclosure. In step 92, the user may position the filter in the filtering state in the body vessel. In step 94, the user may allow the second biodegradable material, or the connectors with a second degradation rate, to biodegrade. In step 96, the user may allow the filter to move to the open state. In step 98, the user may allow the first biodegradable material, or the rings with a first degradation rate, to biodegrade. At this point the entire filter has been removed from the body to avoid unintended consequences.

Finally, further embodiments of devices in accordance with the principles of the present disclosure are described in the non-limiting examples that follow.

Example 1: a device including a superior ring, and inferior ring, and a plurality of connectors in accordance with the principles of the present disclosure is described. The wire of the rings is made of a first alloy having a first ratio of iron to manganese, and the wire of the connectors is made of a second alloy of iron and manganese that has a second ratio of iron to manganese which is different from the first ratio. In such an embodiment, the wire of the rings and the wire of the connectors are substantially equal in thickness or diameter to one another. The unequal iron:manganese alloys are selected such that, when placed in proximity to one another, the alloy of the connectors degrades more quickly than that of the rings after implantation of the device to a body vessel.

Example 2: a device including a superior ring, and inferior ring, and a plurality of connectors in accordance with the principles of the present disclosure is described. The wire of the rings is made an alloy of iron and manganese. The wire of the connectors is made of an alloy of zinc. In such an embodiment, the wire of the rings and the wire of the connectors are substantially equal in thickness or diameter to one another. The anodic character of the zinc-alloy connectors causes them to degrade more quickly than the rings after implantation of the device to a body vessel.

Example 3: a device including a superior ring, and inferior ring, and a plurality of connectors in accordance with the principles of the present disclosure is described. The wire of the rings and of the connectors is an alloy of iron and manganese. The diameter of the wire that makes up the connectors is about 75% of the diameter of the wire that makes up the rings. The lower thickness of the connectors means that degradation will proceed to completion more quickly than the rings after implantation of the device to a body vessel owing to the smaller mass of the connectors relative to the rings.

Example 4: a device including a superior ring, and inferior ring, and a plurality of connectors in accordance with the principles of the present disclosure is described. The wire of the rings and of the connectors is an alloy of iron and manganese. The wire for the connectors has a surface that undergoes etching or grinding prior to assembly of the device, or prior to implantation of the device, in order to remove any oxide layer that may have formed on the connectors, or to decrease the thickness of the connectors, or both. The treatment of the connectors causes them to degrade more quickly than the rings after implantation of the device to a body vessel.

It should be understood that the foregoing relates to exemplary embodiments of the disclosure and that modifications may be made without departing from the spirit and scope of the disclosure as set forth in the following claims. While the disclosure has been described with respect to certain embodiments it will be appreciated that modifications and changes may be made by those skilled in the art without departing from the spirit of the disclosure.

The invention claimed is:

1. A filter for use in a body vessel, the filter defining a longitudinal axis therethrough and comprising:
   a superior ring comprising a plurality of superior struts having a first superior strut extending to a second superior strut, defining a first superior valley, and a third superior strut extending to a fourth superior strut, defining a second superior valley, the superior ring having first superior valleys alternating with second superior valleys;
   an inferior ring comprising a plurality of inferior struts having a first inferior strut extending to a second inferior strut, defining a first inferior peak, and a third inferior strut extending to a fourth inferior strut, defining a second inferior peak, the inferior ring having first inferior peaks alternating with second inferior peaks;
   a plurality of connectors extending between the superior and inferior rings, each connector having a first end extending to a second end with a central region therebetween, the plurality of connectors cross each other at their respective central regions, each first superior valley having one first end attached to and parallel with the first superior strut and extending to the second end being attached to and parallel with one second inferior strut; and
   the plurality of connectors having a degradation rate greater than that of the superior ring and that of the inferior ring such that the filter has a filtering state and an open state, the first and second superior valleys and first and second inferior peaks extending radially toward the longitudinal axis in the filtering state, and the first and second superior valleys and the first and second inferior peaks contacting the body vessel in the open state.

2. The filter of claim 1 wherein the superior and inferior rings comprise a first biodegradable material having a first degradation rate and the plurality of connectors comprise a second biodegradable material having a second degradation rate, the second degradation rate being greater than the first degradation rate.

3. The filter of claim 2 wherein the connectors galvanically protect the superior ring and the inferior ring from degradation.

4. The filter of claim 1 wherein the superior and inferior rings comprise a first biodegradable material having a first size and the plurality of connectors comprise the first biodegradable material having a second size wherein the second size is smaller than the first size, the plurality of connectors degrading before the superior and inferior rings to move the filter from the filter state to the open state.

5. The filter of claim 1 wherein the plurality of connectors are laced with each other at the respective central regions such that a first connector moves relative to a second connector.

6. The filter of claim 1 wherein the plurality of connectors are immobilized relative to each other at the respective central regions such that a first connector does not move relative a second connector.

7. The filter of claim 6 wherein the connectors are immobilized by bonding.

8. The filter of claim 2 wherein the first biodegradable material comprises an alloy comprising at least one selected from the group consisting of magnesium, manganese, iron, calcium, zinc, and a rare earth metal.

9. The filter of claim 1, wherein at least one surface of at least one connector is treated by at least one method selected from the group consisting of etching and grinding.

10. The filter of claim 1 wherein the first superior strut and the second superior strut each having a first superior length, the third superior strut and the fourth superior strut each having a second superior length such that the first superior length is greater than the second superior length.

11. The filter of claim 1 wherein the first inferior strut and the second inferior strut each having a first inferior length, the third inferior strut and the fourth inferior strut each having a second inferior length such that the first inferior length is greater than the second inferior length.

12. The filter of claim 1 wherein the first superior valleys extend a first distance toward the respective central regions in the filtering state and the second superior valleys extend a second distance toward the respective central regions in the filtering state such that the first distance is less than the second distance.

13. The filter of claim 1 wherein the first inferior peaks extend a third distance toward the respective central regions in the filtering state and the second inferior peaks extend a fourth distance toward the respective central regions in the filtering state such that the third distance is less than the fourth distance.

14. The filter of claim 1, wherein the plurality of connectors is are in contact with one another at their respective central regions.

15. A filter for use in a body vessel, the filter defining a longitudinal axis therethrough and comprising:
   a superior ring comprising a plurality of superior struts having a first superior strut extending to a second superior strut, defining a first superior valley, and a third superior strut extending to a fourth superior strut, defining a second superior valley, the superior ring having first superior valleys alternating with second superior valleys and having a first degradation rate, the first superior strut and the second superior strut each having a first superior length, the third superior strut and the fourth superior strut each having a second superior length such that the first superior length is greater than the second superior length;

an inferior ring comprising a plurality of inferior struts having a first inferior strut extending to a second inferior strut, defining a first inferior peak, and a third inferior strut extending to a fourth inferior strut, defining a second inferior peak, the inferior ring having first inferior peaks alternating with second inferior peaks and having the first degradation rate, the first inferior strut and the second inferior strut each having a first inferior length, the third inferior strut and the fourth inferior strut each having a second inferior length such that the first inferior length is greater than the second inferior length; and a plurality of connectors extending between the superior and inferior rings and having a second degradation rate, each connector having a first end extending to a second end with a central region therebetween, the plurality of connectors being in contact with each other at the respective central regions and moving the filter between a filtering state and an open state, the first and second superior valleys and first and second inferior peaks extending radially toward the longitudinal axis in the filtering state, and the first and second superior valleys and first and second inferior peaks contacting the body vessel in the open state.

16. The filter of claim 15 wherein the plurality of connectors are laced with each other at the respective central regions such that a first connector moves relative to a second connector.

17. The filter of claim 15 wherein the plurality of connectors are immobilized relative to each other at the respective central region such that a first connector does not move relative to a second connector.

18. The filter of claim 17 wherein the connectors are immobilized by bonding.

19. The filter of claim 15 wherein the first superior valleys extend a first distance toward the longitudinal axis in the filtering state and the second superior valleys extend a second distance toward the longitudinal axis in the filtering state such that the first distance is less than the second distance.

20. The filter of claim 15 wherein each first superior valley has one first end attached to and parallel with the first superior strut and extending to the second end being attached to and parallel with one second inferior strut.

21. An assembly for use in a body vessel, the assembly comprising:

an outer sheath having a body extending from a proximal part to a distal part, the body being tubular and forming a lumen extending therethrough;

an inner member extending from a proximal portion to a distal portion, the inner member being disposed within the lumen and slidably movable relative to the outer sheath; and a filter being removably coupled to the distal portion, the filter defining a longitudinal axis therethrough and comprising:

a superior ring comprising a plurality of superior struts having a first superior strut extending to a second superior strut, defining a first superior valley, and a third superior strut extending to a fourth superior strut, defining a second superior valley, the superior ring having first superior valleys alternating with second superior valleys and having a first degradation rate;

an inferior ring comprising a plurality of inferior struts having a first inferior strut extending to a second inferior strut, defining a first inferior peak, and a third inferior strut extending to a fourth inferior strut, defining a second inferior peak, the inferior ring having first inferior peaks alternating with second inferior peaks and having the first degradation rate;

a plurality of connectors extending between the superior and inferior rings and having a second degradation rate, each connector having a first end extending to a second end with a central region therebetween, the plurality of connectors being in contact with each other at the respective central regions, each first superior valley having one first end attached to and parallel with the first superior strut and extending to the second end being attached to and parallel with one second inferior strut; and the second degradation rate being faster than the first degradation rate such that the filter has a filtering state and an open state, the first and second superior valleys and first and second inferior peaks extending radially toward the longitudinal axis in the filtering state, and the first and second superior valleys and the first and second inferior peaks contacting the body vessel in the open state.

* * * * *